United States Patent
Bjorkesten et al.

(10) Patent No.: US 11,237,130 B2
(45) Date of Patent: Feb. 1, 2022

(54) METHOD FOR DETERMINING A SIZE OF BIOMOLECULES

(71) Applicant: Cytiva Sweden AB, Uppsala (SE)

(72) Inventors: Lennart Bjorkesten, Storvreta (SE); Nils Stafstrom, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 364 days.

(21) Appl. No.: 15/738,361

(22) PCT Filed: Jun. 30, 2016

(86) PCT No.: PCT/EP2016/065379
§ 371 (c)(1),
(2) Date: Dec. 20, 2017

(87) PCT Pub. No.: WO2017/001597
PCT Pub. Date: Jan. 5, 2017

(65) Prior Publication Data
US 2018/0172630 A1    Jun. 21, 2018

(30) Foreign Application Priority Data
Jul. 1, 2015  (GB) ..................................... 1511508

(51) Int. Cl.
*G01N 27/447*  (2006.01)
*G01N 30/86*   (2006.01)
(Continued)

(52) U.S. Cl.
CPC ... *G01N 27/44726* (2013.01); *G01N 21/6428* (2013.01); *G01N 27/44717* (2013.01);
(Continued)

(58) Field of Classification Search
CPC ................. G01N 27/447; G01N 27/26; G01N 27/44769; G01N 27/44717;
(Continued)

(56) References Cited

U.S. PATENT DOCUMENTS

| 4,997,537 A | 3/1991 | Karger et al. |
| 5,119,315 A * | 6/1992 | Kemp ................ G01N 30/8665 702/27 |

(Continued)

FOREIGN PATENT DOCUMENTS

| JP | 2000088831 A | 3/2000 |
| WO | 00/16087 A1 | 3/2000 |

(Continued)

OTHER PUBLICATIONS

Chinese Office Action for CN Application No. 201680038600.4 dated Jul. 4, 2019 (7 pages).
(Continued)

*Primary Examiner* — Gurpreet Kaur
(74) *Attorney, Agent, or Firm* — Eversheds Sutherland (US) LLP

(57) ABSTRACT

The present invention relates to a method for determining size of biomolecules separated in a medium by an electric field using marker molecules of known size, comprising —(101) detecting a plurality of bands and forming a detected marker sequence and a detected unknown sequence based on a separation criterion, —(102) determining band properties for each detected band, —(103) comparing the band properties of the detected bands of the detected marker sequence with known band properties for a plurality of marker molecules forming a known marker sequence and assigning a score to each comparison, said score being based on at least one of relative distance, relative intensity, expected distance and expected intensity between bands, —(104) selecting the comparison with the highest score and associating all or a subset of the detected bands of the detected marker sequence with said plurality of marker molecules of the known marker sequence in accordance with said comparison to determine size of the all or a subset of the detected marker sequence, and —(105) comparing the bands (Continued)

Figure 1:
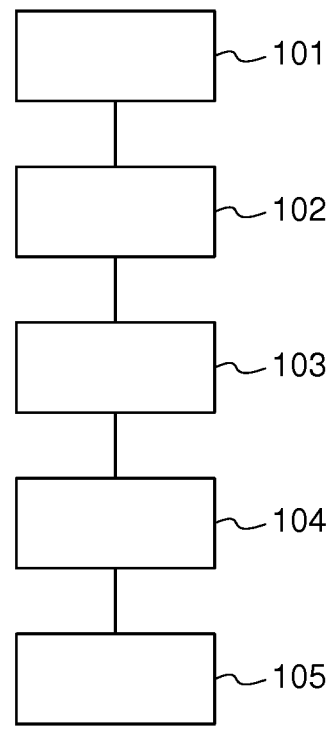

of the detected marker sequence with the bands of the detected unknown sequence to determine a size of biomolecules for each identified band of the detected unknown sequence based on the known sizes of the marker molecules. The invention also relates to software configured to perform the method and to a computer readable medium for storing said software.

5 Claims, 3 Drawing Sheets

(51) Int. Cl.
G01N 21/64 (2006.01)
G06F 17/15 (2006.01)

(52) U.S. Cl.
CPC ... *G01N 27/44752* (2013.01); *G01N 30/8693* (2013.01); *G06F 17/15* (2013.01); *C12Q 2600/166* (2013.01)

(58) Field of Classification Search
CPC ......... G01N 27/44726; G01N 30/8693; G01N 30/8668; B01L 2400/01415; B01L 2400/0421; B01L 3/502753; B01D 57/02
See application file for complete search history.

(56) References Cited

U.S. PATENT DOCUMENTS

| | | |
|---|---|---|
| 7,708,870 B2 | 5/2010 | Tabuchi et al. |
| 2006/0027744 A1* | 2/2006 | Stults ..................... G01N 33/50 250/288 |
| 2006/0194329 A1* | 8/2006 | Ogiwara ................. G16C 20/20 436/89 |
| 2008/0234945 A1* | 9/2008 | Walk ................... G01N 30/8668 702/19 |
| 2011/0184648 A1* | 7/2011 | Gorenstein ............ G01N 30/72 702/19 |
| 2014/0324373 A1 | 10/2014 | Xiang et al. |
| 2015/0355141 A1 | 12/2015 | Tonson et al. |

FOREIGN PATENT DOCUMENTS

| | | |
|---|---|---|
| WO | 02/08949 A2 | 1/2002 |
| WO | 2004/053153 A1 | 6/2004 |
| WO | 2008/045136 A2 | 4/2008 |

OTHER PUBLICATIONS

PCT International Search Report and Written Opinion for PCT Application No. PCT/EP2016/065379 dated Nov. 7, 2016 (15 pages).
GB Search Report for GB Application No. 1511508.2 dated Dec. 17, 2015 (4 pages).
Japanese Office Action for JP Application No. 2017-567337 dated May 25, 2020 (10 pages with English translation).

* cited by examiner

METHOD FOR DETERMINING A SIZE OF BIOMOLECULES

CROSS REFERENCE TO RELATED APPLICATIONS

This application claims the priority benefit of PCT/EP2016/065379 filed on Jun. 30, 2016 which claims priority benefit of Great Britain Application No. 1511508.2 filed Jul. 1, 2015. The entire contents of which are hereby incorporated by reference herein.

TECHNICAL FIELD

The present invention relates to a method for determining a size of biomolecules separated in a medium by an electric field using marker molecules of known size.

BACKGROUND

In many technical fields, it is important to correctly identify biomolecules contained in a sample. This can be performed through a number of different separation and detection methods for different classes of biomolecules in various separation media.

One known way is through electrophoresis, a commonly used technique for the analysis the protein content in a sample.

Electrophoresis is a separation technique based on the mobility of charged molecules in an electric field. It is used mainly for the analysis and purification of large molecules such as proteins or nucleic acids. Electrophoresis is normally carried out by loading a sample containing the molecules of interest into a well in a porous matrix to which a voltage is then applied. Differently sized, shaped, and charged molecules in the sample move through the matrix at different velocities. At the end of the separation, the molecules are detected as bands at different positions in the matrix. The matrix can be composed of a number of different materials, including paper, cellulose acetate, or gels made of polyacrylamide, agarose, or starch. In polyacrylamide and agarose gels, the matrix can also act as a size-selective sieve in the separation.

Thus, different proteins migrate at different speed in a gel depending on size and charge when an electric field is applied. Two or more samples may be separated in the same gel. The samples are distinguished from each other by being separated in separate lanes or by different labeling. It is often essential to being able to assign a size to the separated protein components. This can be done by loading dedicated size marker proteins of known size in the same or in separate lanes in the gel. The position of these size marker proteins after the electrophoresis separation has taken place yields a size scale by which the proteins of unknown size can be assigned a size using a calibration procedure by assigning a size calibration curve. The position in the gel of the marker proteins along the separation direction is plotted as a function of the known size and a calibration curve resulting from a fit to these data points is then used to calibrate the size of the proteins of unknown size. Further information regarding the general background to the field of electrophoresis can be found in WO2013180642, US2003221963 or WO2015079048 by the same applicant.

One common problem of electrophoresis is that contaminations in the gel can be mistaken for some of the reference molecules, resulting in a faulty identification of reference molecules and hindering the accurate comparison of size between these and the unknown biomolecules. Generally, an operator is needed for assessing the results and removing faulty data to improve the identification and size assessments.

Similar technology is disclosed by U.S. Pat. No. 5,273,632, WO2005/015199 and U.S. Pat. No. 4,720,786.

There is thus a need for an improved method for correctly identifying unknown biomolecules.

DISCLOSURE OF THE INVENTION

The object of the present invention is to eliminate or at least to minimize the problems described above. This is achieved through a method according to the appended independent claims, providing an improved method for identifying unknown biomolecules, either by detecting a plurality of bands and forming a detected marker sequence and a detected unknown sequence based on a separation criterion,
  determining band properties for each detected band,
  comparing the band properties of the detected bands of the detected marker sequence with known band properties for a plurality of marker molecules forming a known marker sequence and assigning a score to each comparison, said score being based on at least one of relative distance, relative intensity, expected distance and expected intensity between bands,
  selecting the comparison with the highest score and associating all or a subset of the detected bands of the detected marker sequence with said plurality of marker molecules of the known marker sequence in accordance with said comparison to determine size of the all or a subset of the detected marker sequence, and
  comparing the bands of the detected marker sequence with the bands of the detected unknown sequence to determine a size of biomolecules for each identified band of the detected unknown sequence based on the known sizes of the marker molecules.

or by detecting a plurality of data points from a lane and creating a detected lane profile,
  creating a previous lane profile based on theoretical data or previously detected data comprising a plurality of marker molecules,
  aligning the detected lane profile to the previous lane profile based on a profile alignment calculation to find a best alignment
  determining size of a plurality of marker molecules in the detected lane profile based on the best alignment of the detected lane profile to the previous lane profile,
  detecting a plurality of data points corresponding to unknown biomolecules from another lane
  determining a size of the unknown biomolecules by correlating the data points corresponding to said unknown biomolecules to the determined size of the plurality of marker molecules.

Thereby, the identification of the marker molecules can be improved and the risk of faulty detection decreased without the need of an operator, thus also improving the determination of size of the biomolecules.

According to an aspect of the invention, the comparison is made by comparing band properties of the detected sequence with known band properties of the known marker sequence and allowing for additional bands or missing bands in the detected sequence but not allowing for changing the order of the bands in the detected sequence. Thereby, the risk of faulty detection is further decreased.

According to yet another aspect of the invention, the band properties of the detected band include at least one of a position and an intensity. Thereby, the relative distance and relative intensity between a detected band and other detected bands, or between a detected band and known band properties of the marker molecules, can be determined and used to in turn determine a score.

According to a further aspect of the invention, the score is determined by comparing relative intensity, relative intensity, expected distance and/or expected intensity of bands of the detected marker sequence with bands of the known marker sequence. Thereby, similarities in these properties between a detected marker band and a known marker band results in a higher score, increasing the possibility of associating the two.

According to yet another aspect of the invention, the separation criterion is that the detected bands are detected in different lanes. Thereby, the detected unknown bands and the detected marker bands can easily be separated and the subsequent analysis and comparison facilitated.

According to a further aspect of the invention, the separation criterion is that the detected bands are of different colors. Thereby, the bands can easily be separated into detected marker bands and detected unknown bands even if they are present in the same lane, provided that the detected marker bands are of one color and the detected unknown bands are of another color. Alternatively, the marker molecules are marked with multiple colors so that each band corresponding to one molecular weight has a high intensity in one color and a low intensity in another, and an adjacent band corresponding to another molecular weight has the opposite distribution of intensity and color. Thus, an intensity ratio can be used to further aid in correctly identifying each band.

According to yet another aspect of the invention, the detected bands of the detected marker sequence are used to create a calibration curve and the size of biomolecules of the detected unknown sequence is determined by comparing band properties of detected bands of the detected unknown sequence with said calibration curve.

Furthermore, according to the invention there is provided a method for determining a quality of size determination of biomolecules, comprising performing the two methods for determining size of biomolecules described herein on the same sample, and comparing the determined size of marker molecules according to the methods to determine a quality of analysis.

Furthermore, it is advantageous to provide software configured to perform the method according to the invention, and to provide a computer readable medium configured to store said software. Many additional advantages and benefits of the invention will become readily apparent in view of the detailed description below.

DRAWINGS

Figure 2:
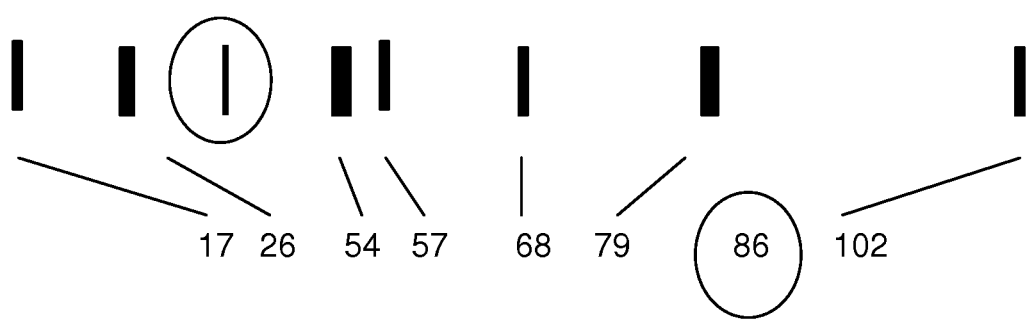
Figure 3:
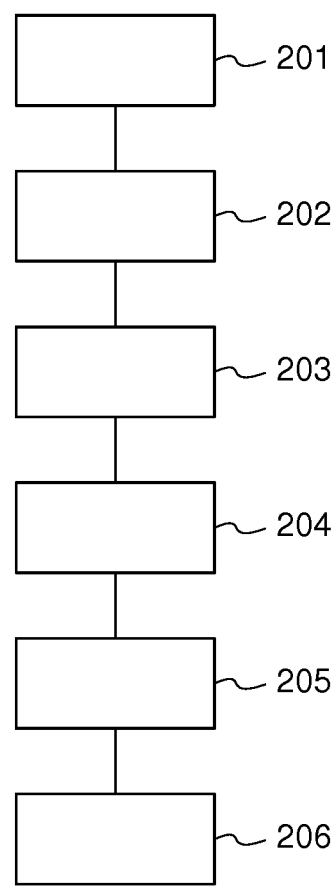
Figure 4:
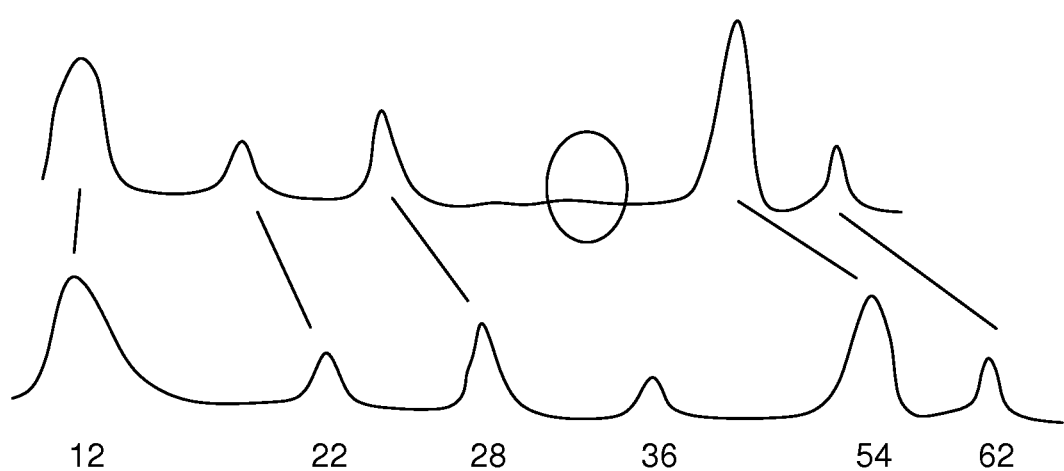
Figure 5A:
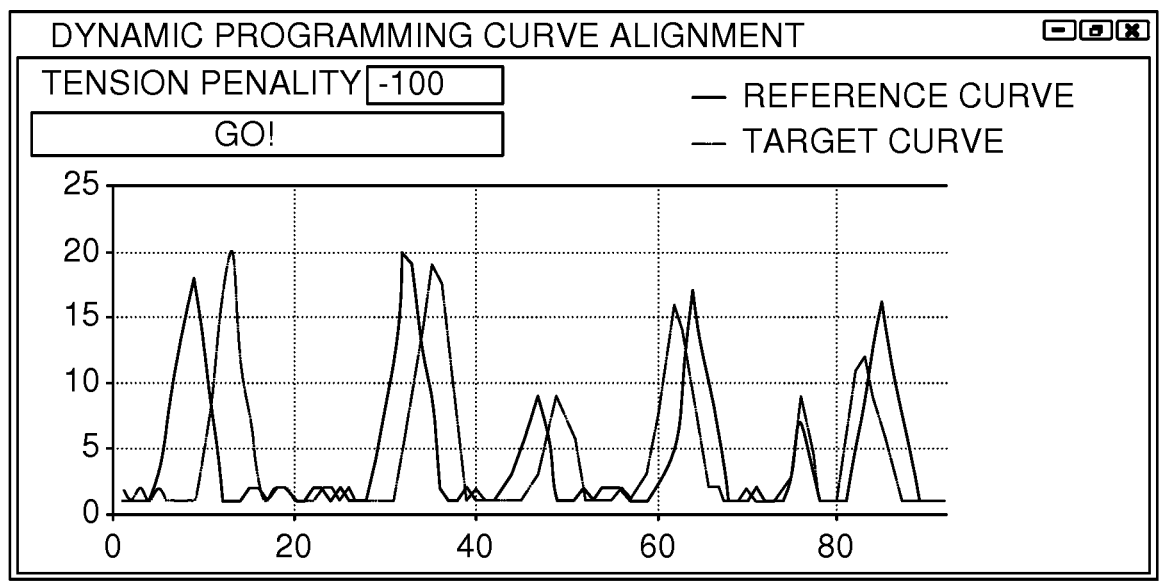
Figure 5B:
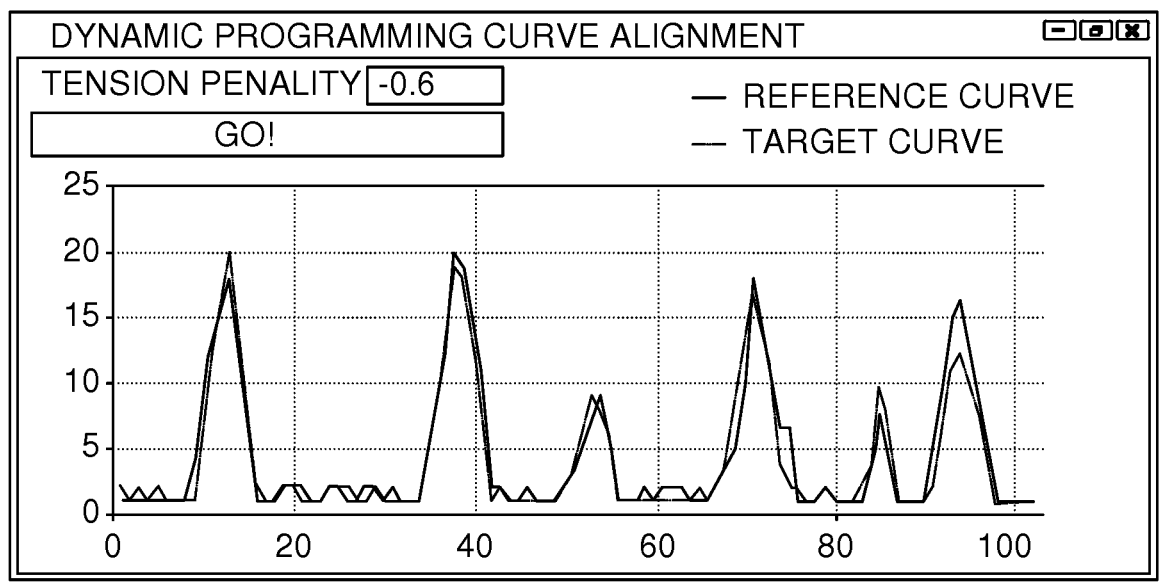

The invention will now be described in more detail with reference to the appended drawings, wherein FIG. 1 discloses a schematic representation of the steps of the method comprising comparing band properties;

FIG. 2 discloses a set of detected bands and a set of values representing known marker molecules;

FIG. 3 discloses a schematic representation of the steps of the method comprising aligning lane profiles;

FIG. 4 discloses a detected lane profile and a previous lane profile corresponding to known marker molecules;

FIG. 5a discloses an implementation of the method comprising aligning lane profiles using dynamic programming with a high penalty; and FIG. 5b discloses an implementation of the method comprising aligning lane profiles using dynamic programming with a low penalty.

DETAILED DESCRIPTION

The methods for determining size of unknown biomolecules are suitable for use with technology for separating molecules of different sizes in a gel or membrane, such as electrophoresis, for instance. In the following, the methods according to the invention will be described with reference to electrophoresis but it is to be understood that they can also be applied to other methods of separating molecules.

Thus, at least one sample containing biomolecules of unknown size and another sample containing a plurality of marker molecules are placed in lanes in a gel. In most cases, the samples are placed in different lanes but they may also be place in the same lane. After being subjected to an electrical field, the biomolecules and the marker molecules have migrated in the gel and their placement can be detected in the form of discrete bands or a plurality of data points. Generally, the marker molecules used for electrophoresis are supplied in different amounts, resulting in bands of different intensity and allowing for the use of both distance or position and intensity when identifying a marker molecule.

FIG. 1 discloses schematically the steps of the method according to a preferred embodiment of the present invention, where band properties are compared to determine a size of unknown biomolecules. Thus, in a first step 101 a plurality of discrete bands are detected and formed into two sequences based on a separation criterion. The separation criterion may be that bands detected in the same lane are gathered in the same sequence whereas bands detected in another lane form another sequence, or may be that bands on one color are placed in one sequence and bands of another color in another sequence. The color used can be of any type, such as fluorescent color, color detectable by infrared or color detectable by visual light, and can be detected by any suitable detection means.

Thereby, the bands can easily be separated into detected marker bands and detected unknown bands even if they are present in the same lane, provided that the detected marker bands are of one color and the detected unknown bands are of another color. Alternatively, the marker molecules are marked with multiple colors so that each band corresponding to one molecular weight has a first intensity in one color and a second intensity in another, one of which first and second intensity being higher than the other and the other being lower, and an adjacent band corresponding to another molecular weight has the opposite distribution of intensity and color. Thus, an intensity ratio can be used to further aid in correctly identifying each band.

Other separation criteria can also be used.

One of the sequences is a detected marker sequence, containing bands that correspond to the sample of marker molecules, and the other is a detected unknown sequence that contains bands that correspond to the sample of biomolecules of unknown size. The bands can be located in just one lane or in a plurality of lanes in the gel, depending on the placement of the samples before application of the electrical field.

In a second step 102, band properties for each detected band are determined. The band properties include information regarding an intensity of the band and/or a location of the band, i.e. the distance from each band to other bands or to a reference. Preferably, the intensity and distance of the plurality of bands can be combined to yield relative intensity and relative distance of bands compared to each other.

In a third step 103, the band properties for each band are compared with known band properties for marker molecules forming a known marker sequence. Preferably, the marker molecules are sorted according to size in the known marker sequence, starting with the largest or the smallest and progressing towards the smallest or the largest, respectively. The known marker sequence thus shows the order in which the marker molecules in the lane should turn up among the detected bands. The known band properties are preferably at least partly the same properties as those determined in the second step 102, to allow for an identification of some of the detected bands of the detected marker sequence with marker molecules in the known marker sequence.

During the comparison in the third step 103, the detected bands are compared to the known marker sequence in such a way as to find a satisfactory match between the detected band sequence and the known marker sequence. This comparison therefore allows for the presence of additional bands or missing bands in the detected band sequence but does not allow for the individual detected bands in the detected band sequence to switch places. Each comparison is awarded a score to reflect how well each detected band corresponds to a marker molecule in the known marker sequence and how well the detected marker sequence comprising the detected band as a whole can be matched to the known marker sequence.

FIG. 2 discloses a comparison between a plurality of detected bands, represented by rectangles of varying width that symbolizes different intensities, and a plurality of known markers, represented by numbers that denote their size in kDa. The score is preferably based on the intensity and placement of the bands, both alone and in combination with each other. Thus, for each band separately, an absolute intensity and an absolute distance the band has traveled in the gel can be used for comparison against the known markers. When combining the band properties of different bands, a relative distance between the distance each band has traveled in the gel and a relative intensity, i.e. the intensity of one band compared to the intensity of another, can also be determined and used for the comparison.

Depending on how well the absolute an relative properties of a detected band in the detected marker sequence matches the known properties of the known marker sequence, a score is awarded. The order of the bands in both the detected marker sequence and the known marker sequence is maintained, since the likelihood that two bands would switch places with each other is very low. However, due to contamination of the gel, gel properties and other factors, it is possible that a band has been detected that does not in fact correspond to a marker molecule (shown by a ring around a band in FIG. 2), or that a marker molecule has failed to be detected as a discrete band (shown by a ring around the number denoting a marker molecule in FIG. 2). Therefore, when performing the comparison, this is taken into account when awarding a score.

In a fourth step 104, the comparison with the highest score is selected. This comparison denotes which of the bands of the detected marker sequence that correspond to bands in the known marker sequence and which of them corresponds to which marker molecule. In general, only a subset of the detected bands will be seen as corresponding to the marker molecules and the rest are contaminations or the like. This subset of bands is then associated with the marker molecules in accordance with the comparison.

In a fifth step 105, bands in the detected unknown sequence are analyzed. Based on their band properties and especially the relative distance between them and bands that have been associated with marker molecules, a size of the biomolecules corresponding to the bands can be determined. In some embodiments, the identified marker molecules of the detected marker sequence are used to create a calibration curve and the size of the biomolecules in each band of the detected unknown sequence are identified through comparison with this curve.

Thanks to the method according to the invention, the samples can be provided in the same lane or in different lanes and can still be correctly identified as either marker molecules or unknown biomolecules thanks to the use of separation criteria. It is also possible to disregard contaminations that result in additional bands and might otherwise be mistaken for marker molecules.

An alternative method according to another preferred embodiment of the invention is disclosed by FIG. 3-5, where a plurality of data points are detected from a lane in a first step 201 and used to create a detected lane profile, plotting signal intensity as a function of separation distance.

In a second step 202, a previous lane profile is created based either on theoretical data giving an artificial size marker lane profile or on previously detected data giving an experimental size marker lane profile. The previous lane profile comprises data corresponding to a plurality of marker molecules of known size and intensity, similar to the known band properties discussed above with reference to FIG. 1-2.

In a third step 203, the detected lane profile is aligned to the previous lane profile based on a profile alignment calculation to find the best alignment. FIG. 4 discloses an example of a detected lane profile, in the upper part of the Figure, and a previous lane profile and numbers in a lower part of the Figure. Each type of molecules in the gel has given rise to one peak in the detected lane profile, but a difference from the previously described method disclosed by FIG. 1-2 is that they now each have a peak shape that gives additional information regarding the properties of the marker molecules. By aligning the lane profiles with each other, this additional information is used to further improve the identification of marker molecules. It is still possible that marker molecules in the detected lane profile are missing, such as is shown by the ring on the detected lane profile, or that additional peaks appear that do not match any of the marker molecules, and therefore this is taken into account when aligning the profiles.

The profile alignment calculation can be based on any suitable method to compare one profile to another and align them in the best possible way, but is preferably based on parameterized shifts, expansions or compressions to process the data and align the profiles. In order to identify one alignment as a best alignment, correlation such as Pearson correlation is used. Alternatively, the profile alignment calculation can be based on dynamic programming, introducing a penalty for generating gaps in the curves.

FIG. 5a-5b shows an example of aligning the lane profiles using dynamic programming. In FIG. 5a, a high penalty is used, resulting in a very poor aligning of the curves. In FIG. 5b, on the other hand, a low penalty is used, allowing for a very good fitting of the curves.

In a fourth step 204, a size of a plurality of marker molecules in the detected lane profile is determined based on the best alignment of the detected lane profile to the previous lane profile. Thus, the best alignment allows for an identification of the marker molecules and provides a size reference for the subsequent size determination of unknown biomolecules in other lanes.

In a fifth step 205, a plurality of data points corresponding to unknown biomolecules in another lane are detected, and in a sixth step 206, a size of the unknown biomolecules is determined by correlating the data points corresponding to said unknown biomolecules to the determined size of the plurality of marker molecules.

The methods described above may also be used independently on the same gel, in such a way that a plurality of detected bands and a detected lane profile are made and the scoring and aligning performed to identify marker molecules. The results can then be compared to create an assessment of the quality of the analysis according to the method of FIGS. 1-2 and of FIGS. 3-5. If both methods generate the same identification of marker molecules independent of each other, it follows that the quality is good, whereas differences may be interpreted as low quality analysis. For cases where it is determined that the quality is low, a signal can be generated to an operator that a manual assessment is required or that the analysis should be performed again and may yield a different result.

In order to further facilitate the identification of marker molecules using either of the methods disclosed above, it is also possible to use two colors and alternating the intensity of adjacent marker molecules. Thus, two separate sets of bands or peaks can be analyzed independently of each other, or the two sets can be combined to form a ratio for improved identification of each marker molecule. It would also facilitate the analysis to mark each marker molecule with one, two or more colors and the ratios between different color signals are used to make it easier to identify these markers.

The steps of the method are suitably executed by means of a software that is stored in a computer readable medium such as a hard drive, CD rom, USB or the like.

It is to be noted that the steps according to the methods may in some cases be performed in different order and some steps can be performed simultaneously without departing from the scope of the appended claims.

The invention claimed is:

1. Method for determining a size of unknown biomolecules separated in a medium by an electric field using marker molecules of known size, comprising
   detecting a plurality of data points from a lane and creating a detected lane profile,
   creating a previous lane profile based on theoretical data or previously detected data comprising a plurality of marker molecules,
   aligning the detected lane profile to the previous lane profile based on a profile alignment calculation to find a best alignment, wherein the profile alignment calculation is based on at least one of expansions and compressions, wherein the profile alignment calculation is further based on dynamic programming that introduces a penalty for adjusting one or more gaps between at least two peaks of the detected lane profile,
   determining size of a plurality of marker molecules in the detected lane profile based on the best alignment of the detected lane profile to the previous lane profile,
   detecting a plurality of data points corresponding to the unknown biomolecules, and
   determining the size of the unknown biomolecules by correlating the data points corresponding to said unknown biomolecules to the determined size of the plurality of marker molecules.

2. Method according to claim 1, wherein said plurality of data points comprise information of at least one of an intensity and a distance.

3. Method according to claim 1, wherein the best alignment is determined through a comparison using correlation, preferably Pearson correlation.

4. Software configured to perform the method according to claim 1.

5. Computer readable medium configured to store the software according to claim 4.

* * * * *